(12) United States Patent
Dirkzwager et al.

(10) Patent No.: US 7,674,940 B2
(45) Date of Patent: *Mar. 9, 2010

(54) PROCESS FOR THE PREPARATION OF DETERGENT COMPOUNDS

(75) Inventors: Henk Dirkzwager, Amsterdam (NL); Robert Martijn Van Hardeveld, Amsterdam (NL); Arend Hoek, Amsterdam (NL); Peter William Lednor, Amsterdam (NL); Joannes Ignatius Geijsel, The Hague (NL)

(73) Assignee: Shell Oil Company, Houston, TX (US)

( * ) Notice: Subject to any disclaimer, the term of this patent is extended or adjusted under 35 U.S.C. 154(b) by 1237 days.

This patent is subject to a terminal disclaimer.

(21) Appl. No.: 10/546,281

(22) PCT Filed: Feb. 19, 2004

(86) PCT No.: PCT/EP2004/050153

§ 371 (c)(1),
(2), (4) Date: Aug. 19, 2005

(87) PCT Pub. No.: WO2004/074407

PCT Pub. Date: Sep. 2, 2004

(65) Prior Publication Data

US 2006/0149117 A1 Jul. 6, 2006

(30) Foreign Application Priority Data

Feb. 20, 2003 (EP) .................................. 03251039

(51) Int. Cl.
*C07C 2/00* (2006.01)
*C07C 4/00* (2006.01)
*C07C 6/00* (2006.01)
*C11D 17/00* (2006.01)

(52) U.S. Cl. ..................... 585/323; 510/357; 518/700

(58) Field of Classification Search ................ 585/323; 510/357; 518/700
See application file for complete search history.

(56) References Cited

U.S. PATENT DOCUMENTS

| 1,261,040 | A | 4/1918 | Lanes |
| 3,239,455 | A | 3/1966 | Lickus et al. ................ 208/212 |
| 3,674,885 | A | 7/1972 | Griesinger et al. ...... 260/671 B |
| 3,892,252 | A | 7/1975 | Poettmann ................... 137/13 |
| 4,594,172 | A | 6/1986 | Sie ............... 252/55 |
| 6,392,109 | B1 | 5/2002 | O'Rear et al. ............... 585/323 |
| 7,282,474 | B2 | 10/2007 | Dirkzwager et al. ........ 510/357 |
| 2002/0128530 | A1 | 9/2002 | Miller et al. ................ 585/517 |

FOREIGN PATENT DOCUMENTS

| AU | 698392 | 10/1998 |
| GB | 990744 | 4/1965 |
| WO | 99/34917 | 7/1999 |
| WO | 99/59942 | 11/1999 |
| WO | 02/100806 | 12/2002 |

OTHER PUBLICATIONS

International Search Report and Written Opinion mailed Jun. 23, 2004.
Detergent Manufacture Including Zeolite Builders and Other New Materials, Chemical Technology Review; No. 128. Ed M. Sittig, Noyes Data Corp., NJ 1979.

*Primary Examiner*—In Suk Bullock

(57) ABSTRACT

A process for the preparation of detergents containing a relatively low amount of isoparaffins, involving separating a hydrocarbonaceous product stream from a Fischer-Tropsch process using a cobalt based catalyst and producing normally liquid and normally solid hydrocarbons into a light fraction boiling below an intermediate fraction having detergent hydrocarbons, an intermediate boiling fraction having detergent hydrocarbons and a heavy fraction boiling above the intermediate boiling fraction having detergent hydrocarbons, followed by conversion of the detergent hydrocarbons present in the intermediate boiling fraction into detergents, the Fischer-Tropsch process being carried out at a relatively high pressure.

15 Claims, No Drawings

US 7,674,940 B2

PROCESS FOR THE PREPARATION OF DETERGENT COMPOUNDS

PRIORITY CLAIM

The present application claims priority on European Patent Application 03251039.8 filed 20 Feb. 2003.

FIELD OF THE INVENTION

The invention relates to a process for the preparation of detergents with a relatively low amount of isoparaffins, wherein the detergent is derived from a Fischer-Tropsch hydrocarbonaceous product stream.

BACKGROUND OF THE INVENTION

The Fischer-Tropsch process is well known in the art. Synthesis gas, a mixture of hydrogen and carbon monoxide, is converted over a catalyst usually comprising a Group VIII metal or metal compound at elevated temperature and usually elevated pressure into mainly paraffinic and/or olefinic hydrocarbons and water. Depending on the reaction conditions (temperature, pressure, catalyst, $H_2/CO$ ratio, GHSV etc.) the product properties (e.g. the $C_5^+$ selectivity, the olefin content, the oxygenate content etc.) may vary. At the present moment there is a clear interest in the use of cobalt based catalyst at a temperature between 180 and 270° C. to make mainly very heavy paraffins comprising a major amount of normally solid hydrocarbons. In such Fischer-Tropsch processes substantial amounts of detergent hydrocarbons are produced, i.e. compounds having suitably 9 to 18 carbon atoms, preferably 10 to 17 carbon atoms.

The preparation of detergents, especially biodegradable detergents, from linear olefins prepared in a Fischer-Tropsch process has been described in the literature. For instance, in ACS Symp. Series No. 238, 18-33 (191 ACS Nat. Meeting Div. Pet. Chem. Symp. New York, 13-18 Apr. 1986) it has been described that $C_9$-$C_{15}$ cuts of low and high temperature Fischer-Tropsch processes are suitable feedstocks in the alkylation of benzene to prepare alkylbenzenes, followed by sulfonation and neutralization to convert the alkylbenzenes into alkylbenzene sulfonates. The direct products of these Fischer-Tropsch processes, using iron based catalysts, comprise rather large amounts of olefins. For instance, the high temperature process results in a product comprising about 70% olefins (60% straight chain product), the low temperature process results in about 25% olefins (linearity 93%). Also, U.S. Pat. No. 3,674,885 describes the use of paraffin-olefin mixtures synthesized in a Fischer-Tropsch process in the alkylation of benzene. The paraffins are separated from the alkylation mixture and are recycled to a chlorination unit from which the paraffin-chloroparaffin effluent mixture is combined with the fresh Fischer-Tropsch olefin-paraffin mixture and the combined feeds are used to alkylate the benzene. Detergents may also be made directly from paraffins as described in WO 99/59942.

There exists a clear commercial demand for linear hydrocarbons for the preparation of detergents. In general, the more linear the product, the higher the demand. See for instance U.S. Pat. No. 6,392,109 column 1, lines 12 and 13, and lines 28 to 31, clearly indicating that linear detergent hydrocarbon are preferred over branched detergent hydrocarbons. Thus, there is a clear need for detergent hydrocarbons with a (very) low amount of branched hydrocarbons. It has now been found that when carrying out a Fischer-Tropsch reaction using a cobalt based catalyst the amount of branched hydrocarbons decreases at higher pressures. Thus, when using the same reaction temperature, at higher pressures less branching occurs, at lower pressure more branching occurs.

SUMMARY OF THE INVENTION

The present invention thus is directed to a process for the preparation of detergents containing a relatively low amount of isoparaffins, comprising separating a hydrocarbonaceous product stream, suitably having a boiling range starting with a temperature below the boiling range of detergent hydrocarbons up to a temperature above the boiling range of detergent hydrocarbons, from a Fischer-Tropsch process using a cobalt based catalyst and producing normally liquid and normally solid hydrocarbons into a light fraction boiling below an intermediate fraction comprising detergent hydrocarbons, an intermediate boiling fraction comprising detergent hydrocarbons and a heavy fraction boiling above the intermediate boiling fraction comprising detergent hydrocarbons, followed by conversion of the detergent hydrocarbons present in the intermediate boiling fraction into detergents, the Fischer-Tropsch process being carried out at a pressure above 25 bara.

The invention is further directed to a process for the preparation of detergents containing a relatively low amount of isoparaffins, in which process detergent hydrocarbons present in an intermediate boiling fraction, which fraction has been obtained by separating the hydrocarbonaceous products stream from a Fischer-Tropsch process using a cobalt based catalyst and producing normally liquid and normally solid hydrocarbons into a light fraction boiling below an intermediate fraction comprising detergent hydrocarbons, an intermediate boiling fraction comprising detergent hydrocarbons and a heavy fraction boiling above the intermediate boiling fraction comprising detergent hydrocarbons, the Fischer-Tropsch process being carried out at a pressure above 25 bara, are converted into detergents.

DETAILED DESCRIPTION OF THE INVENTION

The present invention is directed to a process for the preparation of detergents with a relatively low amount of isoparaffins, comprising separating a hydrocarbonaceous product stream, the hydrocarbonaceous product stream having a boiling range starting with a temperature below the boiling range of detergent hydrocarbons up to a temperature above the boiling range of detergent hydrocarbons, from a Fischer-Tropsch process using a cobalt based catalyst and producing normally liquid and normally solid hydrocarbons into a light fraction boiling below an intermediate fraction comprising detergent hydrocarbons, an intermediate boiling fraction comprising detergent hydrocarbons and a heavy fraction boiling above the intermediate boiling fraction comprising detergent hydrocarbons, followed by conversion of the detergent hydrocarbons present in the intermediate boiling fraction into detergents.

The process according to the invention may be carried out at all suitable pressures above 25 bara. Preferably the Fischer-Tropsch process is carried out at a pressure above 35 bara, more preferably above 45 bara, still more preferably above 55 bara. The higher the pressure, the lower less the amount of branched detergent hydrocarbons. A practical upper limit for the Fischer-Tropsch process is 200 bara, preferably the process is carried out at a pressure below 120 bara, more preferably below 100 bara. The Fischer-Tropsch process is suitably a low temperature process carried out at a temperature between 170 and 290° C., preferably at a temperature between 180 and 270° C., more preferably between 200 and 250° C. At higher temperature the conversion of synthesis gas into hydrocarbons is higher, however, the degree of branching (or the formation of iso-paraffins) is also higher. The above indicated temperatures, in combination with a pressure above 25 bara, result in a satisfactory syngas conversion, while branching is still at an acceptable (low) level. The amount of isoparaffins is suitably less than 20 wt % based on the total amount of $C_{10}$ to $C_{18}$ hydrocarbons, especially less than 10 wt %, preferably less than 7 wt %, more preferably less than 4 wt %. The relatively low amount of isoparaffins relates to a decreased amount of isoparaffins produced at pressures above 25 bara when compared with lower pressures. Suitably this means at least 5 mol % less isoparaffin when compared with a pressure of 20 bara.

In the Fischer-Tropsch process a mixture of hydrogen and carbon monoxide is catalytically converted into hydrocarbons and water. The Fischer-Tropsch catalysts are known in the art. Catalysts for use in this process frequently comprise, as the catalytically active component, a metal from Group VIII of the Periodic Table of Elements. Particular catalytically active metals include ruthenium, iron, cobalt and nickel. Cobalt is the catalytically active metal in the process of the present invention. Preferred hydrocarbonaceous feeds are natural gas or associated gas. These feedstocks usually result in synthesis gas having $H_2$/CO ratios of about 2.

The catalytically active metal is preferably supported on a porous carrier. The porous carrier may be selected from any of the suitable refractory metal oxides or silicates or combinations thereof known in the art. Particular examples of preferred porous carriers include silica, alumina, titania, zirconia, ceria, gallia and mixtures thereof, especially silica, alumina and titania.

The amount of catalytically active metal on the carrier is preferably in the range of from 3 to 300 pbw per 100 pbw of carrier material, more preferably from 10 to 80 pbw, especially from 20 to 60 pbw.

If desired, the catalyst may also comprise one or more metals or metal oxides as promoters. Suitable metal oxide promoters may be selected from Groups IIA, IIIB, IVB, VB and VIB of the Periodic Table of Elements, or the actinides and lanthanides. In particular, oxides of magnesium, calcium, strontium, barium, scandium, yttrium, lanthanum, cerium, titanium, zirconium, hafnium, thorium, uranium, vanadium, chromium and manganese are very suitable promoters. Particularly preferred metal oxide promoters for the catalyst used to prepare the hydrocarbons for use in the present invention are manganese and zirconium oxide. Suitable metal promoters may be selected from Groups VIIB or VIII of the Periodic Table. Rhenium and Group VIII noble metals are particularly suitable, with platinum and palladium being especially preferred. The amount of promoter present in the catalyst is suitably in the range of from 0.01 to 100 pbw, preferably 0.1 to 40, more preferably 1 to 20 pbw, per 100 pbw of carrier. The most preferred promoters are selected from vanadium, manganese, rhenium, zirconium and platinum.

The catalytically active metal and the promoter, if present, may be deposited on the carrier material by any suitable treatment, such as impregnation, kneading and extrusion. After deposition of the metal and, if appropriate, the promoter on the carrier material, the loaded carrier is typically subjected to calcination. The effect of the calcination treatment is to remove crystal water, to decompose volatile decomposition products and to convert organic and inorganic compounds to their respective oxides. After calcination, the resulting catalyst may be activated by contacting the catalyst with hydrogen or a hydrogen-containing gas, typically at temperatures of about 200 to 350° C. Other processes for the preparation of Fischer-Tropsch catalysts comprise kneading/mulling, often followed by extrusion, drying/calcination and activation.

The catalytic conversion process may be performed under conventional synthesis conditions known in the art. Typically, the catalytic conversion may be effected at a temperature and pressure as described above. In the catalytic conversion process especially more than 75 wt % of $C_5^+$, preferably more than 85 wt % $C_5^+$ hydrocarbons are formed. Depending on the catalyst and the conversion conditions, the amount of heavy wax ($C_{20}^+$) may be up to 60 wt %, sometimes up to 70 wt %, and sometimes even as much as 85 wt %. Preferably a cobalt catalyst is used, a low $H_2$/CO ratio is used (especially 1.7, or even lower) and a low temperature is used (200-250° C.), in combination with a high pressure. To avoid any coke formation, it is preferred to use an $H_2$/CO ratio of at least 0.6. It is especially preferred to carry out the Fischer-Tropsch reaction under such conditions that the ASF-alpha value (Anderson-Schulz-Flory chain growth factor), for the obtained products having at least 20 carbon atoms, is at least 0.925, preferably at least 0.935, more preferably at least 0.945, even more preferably at least 0.955.

A most suitable catalyst for this purpose is a cobalt-containing Fischer-Tropsch catalyst. Such catalysts are described in the literature, see e.g. AU 698392 and WO 99/34917.

The Fischer-Tropsch process may be a slurry Fischer-Tropsch process, an ebullated bed process or a fixed bed Fischer-Tropsch process, especially a multitubular fixed bed. The product stream of the Fischer-Tropsch process is usually separated into a water stream, a gaseous stream comprising unconverted synthesis gas, carbon dioxide, inert gasses and $C_1$ to $C_3$, and optionally $C_4$, compounds. The full Fischer-Tropsch hydrocarbonaceous product suitably comprises a $C_3$ to $C_{200}$ fraction, preferably $C_4$ to $C_{150}$ fraction. The separation into the one or more light fractions, the intermediate fraction comprising the detergent hydrocarbons and the heavy fraction is suitably done by distillation. Commercially available equipment may be used. The distillation may be carried out at atmospheric pressure, but may also be carried out at reduced pressure. Preferably atmospheric pressure is used to remove the light fraction(s) and vacuum distillation is used to remove the heavy fraction.

The detergent hydrocarbons to be prepared according to the process of the invention, are suitably $C_{10}$ to $C_{18}$ hydrocarbons, preferably $C_{10}$ to $C_{17}$ hydrocarbons, more preferably $C_{10}$ to $C_{13}$ hydrocarbons or more preferably $C_{14}$ to $C_{17}$ hydrocarbons. The use of $C_{10}$ to $C_{17}$ hydrocarbons, especially the $C_{10}$ to $C_{12}$ or the $C_{14}$ to $C_{17}$ hydrocarbons, result in the most suitable detergents.

The intermediate boiling fraction in the process of the present invention suitably comprises at least 80 wt % on total fraction of detergent hydrocarbons, preferably at least 90 wt %, more preferably at least 95 wt %, still more preferably at least 98 wt %. The detergent hydrocarbons consist mainly (i.e. at least 95 wt %) of paraffins (usually between 60 and 95 wt %), olefins (usually between 35 and 5 wt %) and oxygenates (usually mainly alcohols, between 0.1 and 5 wt %). The carbon skeleton of the paraffins, olefins and alcohols are identical, and usually contain between 2 and 20 wt %, more usually between 4 and 14 wt %, of branched carbon chains. Methyl groups, usually forming at least 80% of the branches, more usually at least 90%, are the main form of branches present.

Suitably the light fraction has a boiling range below 150° C., preferably below 160° C., more preferably below 170° C. It is observed that one or more than one light boiling fractions may be removed from the hydrocarbonaceous Fischer-Tropsch stream. All these fractions suitably boil below the above mentioned temperatures. The light fraction may also boil at temperatures higher than mentioned above, but this will result in a loss of detergent hydrocarbons.

Suitably the heavy fraction has a boiling range starting at a temperature above 315° C., preferably above 305° C. It is observed that one or more than one heavy fraction may be removed from the hydrocarbonaceous Fischer-Tropsch stream, suitably all boiling above the temperature mentioned above. The heavy fraction may boil at a lower temperature than the ones mentioned above, but this will result in the loss of detergent hydrocarbons. In another embodiment of the invention the heavy fraction has a boiling range above 250° C., preferably above 240° C. In this way mainly $C_{10}$-$C_{13}$ detergent hydrocarbons are produced.

The intermediate fraction suitably has a boiling range from 170° C. to 315° C., preferably between 170° C. and 240° C. (comprising mainly $C_{10}$-$C_{13}$ detergent hydrocarbons) or preferably between 250° C. and 315° C. (comprising mainly $C_{14}$-$C_{17}$ detergent hydrocarbons).

Very suitably the intermediate fraction comprises at least 80 wt %, preferably at least 90 wt %, more preferably at least 96 wt % based on total weight of the fraction, of detergent hydrocarbons in the range from $C_{10}$ to $C_{18}$ hydrocarbons, preferably $C_{10}$ to $C_{17}$ hydrocarbons, more preferably $C_{10}$ to $C_{13}$ hydrocarbons or more preferably $C_{14}$ to $C_{17}$ hydrocarbons.

The heavy fraction boiling above the intermediate fraction comprising the detergent hydrocarbons is preferably subjected to a hydrocracking process to convert any hydrocarbons present in the fraction boiling above the boiling point of middle distillates into hydrocarbons boiling in the middle distillates boiling range. During the hydrocracking step hydroisomerization will also occur. In the hydrocracking/hydroisomerization step, hydrocarbon fuels are prepared from the hydrocarbon product of the one or more heavy Fischer-Tropsch fractions by hydrocracking and hydroisomerizing the product with hydrogen in the presence of a suitable catalyst. Typically, the catalyst comprises as catalytically active component one or more metals selected from Groups VIB and VIII of the Periodic Table of Elements, in particular one or more metals selected from molybdenum, tungsten, cobalt, nickel, ruthenium, iridium, osmium, platinum and palladium. Preferably, the catalyst comprises one or more metals selected from nickel, platinum and palladium as the catalytically active component. Catalysts comprising platinum as the catalytically active component have been found to be particularly suitable for use in the second hydroconversion stage.

Catalysts for the hydrocracking step typically comprise a refractory metal oxide as a carrier. The carrier material may be amorphous or crystalline. Suitable carrier materials include silica, alumina, silica-alumina, zirconia, titania and mixtures thereof. The carrier may comprise one or more zeolites, either alone or in combination with one or more of the aforementioned carrier materials. Preferred carrier materials for inclusion in the catalyst for use in the process of this invention are silica, alumina and silica-alumina. A particularly preferred catalyst comprises platinum supported on an amorphous silica-alumina carrier.

In the hydrocracking/hydroisomerization stage of this process, the heavy Fischer-Tropsch hydrocarbon product is contacted with hydrogen in the presence of the catalyst at elevated temperature and pressure. Typically, the temperatures necessary to yield the hydrocarbon fuels will lie in the range of from 200 to 400° C., preferably from 275 to 375° C. The pressure typically applied ranges from 20 to 250 bars, more preferably from 40 to 200 bars. Hydrogen may be supplied at a gas hourly space velocity of from 100 to 10000 Nl/l/hr, preferably from 500 to 5000 Nl/l/hr. The hydrocarbon feed may be provided at a weight hourly space velocity of from 0.1 to 5 kg/l/hr, preferably from 0.25 to 2 kg/l/hr. The ratio of hydrogen to hydrocarbon feed may range from 100 to 5000 Nl/kg and is preferably from 250 to 2500 Nl/kg.

The degree of hydrocracking occurring in the hydrocracking/hydroisomerization step may be measured by determining the degree of conversion of the fraction boiling above 370° C. Typically, the hydrocracking/hydroisomerization stage is operated at a conversion of at least 40%.

The hydrocarbon fuel produced in the hydrocracking stage will typically comprise hydrocarbons having boiling points lying in a number of different fuel fractions, for example naphtha, kerosene and gasoil fractions. Separation of the hydrocarbon fuel into the appropriate fractions may be conveniently achieved using distillation techniques well known in the art.

In the process of the invention any reject streams obtained in the above described distillation processes may very suitably be used as additional feedstreams in the process for the preparation of fuels.

In a preferred embodiment of the invention, the hydrocarbonaceous product stream of the Fischer-Tropsch process, more especially the intermediate fraction comprising the detergent hydrocarbons, is hydrogenated before distillation. Any olefins or oxygenates are removed in that way, resulting in an optimum production of detergent hydrocarbons within a narrow carbon distribution range. Further, such hydrogenated fractions are more stable and less corrosive, making transport and/or storage more easy.

In another embodiment of the invention, the intermediate fraction obtained after distillation is hydrogenated before conversion into detergents. Such hydrogenated fractions are more stable and less corrosive, making transport and/or storage more easy. Hydrogenation after distillation avoids the need to hydrogenate a large amount of Fischer-Tropsch product.

The hydrogenation step suitably uses a catalyst comprising molybdenum, tungsten, cobalt, nickel, ruthenium, iridium, osmium, platinum or palladium as a catalytically active metal, preferably one or more of nickel and/or molybdenum, cobalt and/or tungsten, platinum and palladium. The hydrogenation step is suitably carried out at a temperature between 150 and 325° C., preferably between 200 and 275° C., a pressure between 5 and 120 bar, preferably between 20 and 70 bar. Hydrogen may be supplied to the hydroconversion stage at a gas hourly space velocity in the range of from 100 to 10000 Nl/l/hr, more preferably from 250 to 5000 Nl/l/hr. The hydrocarbon product being treated is typically supplied to the hydroconversion stage at a weight hourly space velocity in the range of from 0.1 to 5 kg/l/hr, more preferably from 0.25 to 2.5 kg/l/hr. The ratio of hydrogen to hydrocarbon product may range from 100 to 5000 Nl/kg and is preferably from 250 to 3000 Nl/kg.

Catalysts for use in the hydrogenation step typically comprise a refractory metal oxide or silicate as a carrier. Suitable carrier materials include silica, alumina, silica-alumina, zirconia, titania and mixtures thereof. Preferred carrier materials for inclusion in the catalyst for use in the process of this invention are silica, alumina and silica-alumina.

The catalyst may comprise the catalytically active component in an amount of from 0.05 to 80 parts by weight, preferably from 0.1 to 70 parts by weight, per 100 parts by weight of carrier material. The amount of catalytically active metal present in the catalyst will vary according to the specific metal concerned. One particularly suitable catalyst for use in the first hydroconversion stage comprises nickel in an amount in the range of from 5 to 70 parts by weight per 100 parts by weight of carrier material. A second particularly suitable catalyst comprises platinum in an amount in the range of from 0.05 to 2.0 parts by weight per 100 parts by weight of carrier material.

Suitable catalysts for use in the hydrogenation step of the process of this invention are available commercially, or may be prepared by methods known in the art, for example the methods discussed hereinbefore with reference to the preparation of the hydrocarbon synthesis catalyst.

The hydrogenation step is operated under conditions such that substantially no isomerization or hydrocracking of the feed occurs. The precise operating conditions required to achieve the desired degree of hydrogenation without substantial hydrocracking or hydroisomerization occurring will vary according to the composition of the hydrocarbon product being fed to the hydroconversion stage and the particular catalyst being employed. As a measure of the severity of the conditions prevailing in the hydroconversion stage and, hence, the degree of hydrocracking and isomerization occurring, the degree of conversion of the feed hydrocarbon may be determined. In this respect, conversion, in percent, is defined as the percent weight of the fraction of the feed boiling above 220° C. which is converted during the hydroconversion to a fraction boiling below 220° C. The conversion of the hydroconversion stage is below 20%, preferably below 10%, more preferably below 5%. In the case that there is too much hydroisomerization and/or hydrocracking a decrease of the temperature or the use of a catalyst with a less acidic catalyst function will usually solve the problem.

The detergent hydrocarbons, i.e. the molecules, especially paraffins and/or olefins, having the right number of carbon atoms, are converted into detergents according to methods known in the art. A very suitable method is the alkylation of aromatic compounds with olefins, followed by sulfonation and neutralization. The olefins may be the direct product of the Fischer-Tropsch reaction or obtained after dehydrogenation of paraffins. In the case that the intermediate fraction comprising the detergent hydrocarbons is obtained without any treatment, the olefins present in the fraction may be directly used for conversion into detergents. The remaining paraffins may be dehydrogenated, and the olefins thus obtained may be converted into detergents. Preferably the paraffins, directly obtained in the Fischer-Tropsch process, or obtained after hydrogenation of direct Fischer-Tropsch product, are at least partially catalytically dehydrogenated into mono-olefins before conversion into detergents.

The desired detergent hydrocarbons are then suitably be dehydrogenated. This may be done using processes well known in the art. For instance, the PACOL process of UOP optionally complemented by the DEFINE process of UOP (to convert any dienes in the feed to mono-olefins).

In general, dehydrogenation of the detergent hydrocarbons in the instant process may be accomplished using any of the well-known dehydrogenation catalyst systems or "conventional dehydrogenation catalysts" including those described in "Detergent Manufacture Including Zeolite Builders and Other New Materials", Ed. Sittig, Noyes Data Corp., New Jersey, 1979 and other dehydrogenation catalyst systems, for example those commercially available though UOP Corp. Dehydrogenation may be conducted in the presence of hydrogen gas and commonly a precious metal catalyst is present though alternatively non-hydrogen, precious-metal free dehydrogenation systems such as a zeolite/air system may be used with no precious metals present.

As is well known, dehydrogenation may be complete or partial, more typically partial. Usually between 5 and 50 wt % olefins are formed, suitably between 5 and 20 wt %. When partial, this step forms a mixture of olefin and unreacted paraffin. Such mixture may be a suitable feed for e.g. a benzene alkylation step. After work up of the alkylation step, the unconverted paraffins may be recirculated to the start of the dehydrogenation process.

Suitably the dehydrogenation process uses a catalyst containing molybdenum, tungsten, cobalt, nickel, ruthenium, iridium, osmium, platinum or palladium as a catalytically active metal, preferably one or more of nickel and/or molybdenum, cobalt and/or tungsten, platinum and palladium, more preferably platinum.

The dehydrogenation step may suitably be carried out at a temperature between 300 and 600° C., preferably between 400 and 500° C., a pressure between 0.1 and 20 bar, preferably between 1 and 4 bar.

Following the dehydrogenation, the detergent hydrocarbon may be converted into a detergent according to methods well known in the art. Suitably the reaction is selected from the following reactions:

alkylation with benzene or toluene optionally followed by sulfonation and naturalization;

alkylation with phenol followed by at least one of alkoxylation, sulfonation and, naturalization sulfation and naturalization or alkoxylation combined with oxidation;

hydroformylation optionally followed by at least one of alkoxylation, glycosylation, sulfation, phosphatization or combinations thereof sulfonation;

epoxidation;

hydrobromination followed by amination and oxidation to amine oxide; and phosphonation.

A particularly preferred option is the alkylation of monoaromatic compounds, e.g. benzene, toluene, xylene and mixtures thereof, followed by sulfonation. The alkylation process may use aluminium chloride, hydrogen fluoride, fluoridated zeolites, non-acidic calcium mordenite and the like as catalyst. For example, appropriate process conditions for $AlCl_3$ alkylation are exemplified by a reaction of 5 mole % $AlCl_3$ relative to the detergent hydrocarbon at 100-300° C. for 0.5-1.0 hour in a batch or continuous reactor. Other suitable alkylation catalyst may be selected from shape-selective moderately acidic alkylation catalysts, preferably zeolitic. The zeolite in such catalysts for the alkylation step is preferably selected from the group consisting of mordenite, ZSM-4, ZSM-12, ZSM-20, offretite, gmelinite and zeolite beta in at least partially acidic form. More preferably, the zeolite in the alkylation step is substantially in acid form and is contained in a catalyst pellet comprising a conventional binder and further wherein said catalyst pellet comprises at least about 1%, more preferably at least 5%, more typically from 50% to about 90%, of said zeolite. A commercially available process is the DETAL process.

More generally, a suitable alkylation catalyst is typically at least partially crystalline, more preferably substantially crystalline not including binders or other materials used to form catalyst pellets, aggregates or composites. Moreover the catalyst is typically at least partially acidic. H-form mordenite is an example of a suitable catalyst.

In a preferred embodiment the detergent hydrocarbons are converted into highly linear alcohols according to the process as described in PCT/EPO2/06373.

Beside the above described processes for the preparation of detergents, else other well known processes may also be used.

For instance, the detergent hydrocarbons, especially a preferred range of $C_{14}$-$C_{17}$ detergent hydrocarbons, may be converted into detergents via chlorination or sulfonation of the hydrogenated $C_{14}$-$C_{17}$ stream. Also the preparation of detergents directly from paraffins as described in WO 99/59942 may be used.

In another embodiment the present invention is directed to a process for the preparation of detergent hydrocarbons comprising separating a hydrocarbonaceous product stream comprising detergent hydrocarbons and hydrocarbons boiling above and below the boiling range of the before mentioned detergent hydrocarbons from a Fischer-Tropsch process using a cobalt based catalyst and producing normally liquid and normally solid hydrocarbons into a light fraction boiling below a fraction comprising detergent hydrocarbons, an intermediate boiling fraction comprising detergent hydrocarbons and a heavy fraction boiling above the intermediate boiling fraction comprising detergent hydrocarbons, the Fischer-Tropsch process being carried out at a pressure above 25 bara. In a preferred embodiment the Fischer-Tropsch process is carried out at a pressure above 35 bara, preferably above 45 bara, more preferably above 55 bara. The detergent hydrocarbons are preferably $C_{10}$ to $C_{17}$ hydrocarbons, more preferably $C_{10}$ to $C_{14}$ hydrocarbons. Further, the intermediate boiling fraction comprises at least 80 wt % on total fraction of detergent hydrocarbons, preferably at least 90 wt %, more preferably at least 95 wt %, still more preferably at least 98 wt %. The preferences for this embodiment are the same as for the process as described above.

In this specification the term "mainly" means at least 80 wt %, unless otherwise specified. When an amount of a product or mixture is indicated as "wt %", the percentage is based on the total product stream in which the product is present, unless otherwise specified. Under "normally liquid hydrocarbon product" is meant any product which is at STP (1 bar, 0° C.) a liquid product. For saturated hydrocarbons this means $C_5^+$ hydrocarbons. Under "normally solid product" is meant any product which is solid at STP. For saturated normal hydrocarbons this means $C_{15}^+$. The term $C_n^+$ relates to molecules comprising n carbon atoms or more. The term $C_n^-$ refers to molecules comprising n carbon atoms or less. The term "middle distillates", as used herein, is a reference to hydrocarbon mixtures of which the boiling point range corresponds substantially to that of kerosene and diesel fractions obtained in a conventional atmospheric distillation of crude mineral oil.

EXAMPLE

A cobalt containing Fischer-Tropsch catalyst (12 pbw Co on 100 pbw titania, Mn promoter) was tested at several conditions in the same reactor. The following results were obtained.

| Pressure | 60 bara | 40 bara | 30 bara | 20 bara |
|---|---|---|---|---|
| Temperature | 213° C. | 215° C. | 214° C. | 215° C. |
| STY | 150 | 150 | 100 | 100 |
| i-$C_{12}$ (wt %) | 2.7 | 5.1 | 8.9 | >10 |

STY (space time yield), kg/m³/h. i-$C_{12}$, wt % based on total $C_{12}$ product.

We claim:

1. A process for the preparation of detergents containing a relatively low amount of isoparaffins, comprising separating a hydrocarbonaceous product stream from a Fischer-Tropsch process using a cobalt based catalyst and producing normally liquid and normally solid hydrocarbons into a light fraction boiling below an intermediate fraction comprising detergent hydrocarbons, an intermediate boiling fraction comprising detergent hydrocarbons and a heavy fraction boiling above the intermediate boiling fraction comprising detergent hydrocarbons, followed by converting the detergent hydrocarbons present in the intermediate boiling fraction into detergents, the Fischer-Tropsch process being carried out at a pressure above 25 bara.

2. The process of claim 1, in which the Fischer-Tropsch process is carried out at a pressure above 35 bara.

3. The process of claim 1, in which the detergent hydrocarbons are $C_{10}$ to $C_{17}$ hydrocarbons.

4. The process of claim 1, in which the intermediate boiling fraction comprises at least 80 wt % on total fraction of detergent hydrocarbons.

5. The process of claim 1, in which the light fraction has a boiling range below 150° C. and/or in which the heavy fraction has a boiling range above 315° C.

6. The process of claim 1, in which the intermediate fraction has a boiling range of from 170° C. to 315° C.

7. The process of claim 1, further comprising subjecting the heavy fraction to a hydrocracking process to convert any hydrocarbons present in the fraction boiling above the boiling point of middle distillates into hydrocarbons boiling in the middle distillates boiling range.

8. The process of claim 1, in which the Fischer-Tropsch process is a low temperature process.

9. The process of claim 1, further comprising hydrogenating the hydrocarbonaceous product stream of the Fischer-Tropsch process before distillation.

10. The process of claim 1, further comprising hydrogenating the intermediate fraction obtained after distillation before converting into detergents.

11. The process of claim 9, in which the hydrogenating step uses a catalyst selected from the group consisting of molybdenum, tungsten, cobalt, nickel, ruthenium, iridium, osmium, platinum and palladium as a catalytically active metal, carried out at a temperature between 150 and 325° C.

12. The process of claim 9, in which the hydrogenated intermediate fraction comprising detergent hydrocarbons is at least partially catalytically dehydrogenated into mono-olefins before converting into detergents.

13. The process of claim 1, in which converting the detergent hydrocarbons, optionally after dehydrogenating, into detergents comprises at least one step selected from the group consisting of:
    alkylating with benzene or toluene optionally followed by sulfonating and neutralizing;
    alkylating with phenol followed by at least one step selected from the group consisting of alkoxylating, sulfonating and neutralizing, sulfating and neutralizing and alkoxylating combined with oxidizing;
    hydroformylating optionally followed by at least one step selected from the group consisting of alkoxylating, glycosylating, sulfating, phosphatizing and combinations thereof
    sulfonating;
    epoxidizing;
    hydrobrominating followed by aminating and oxidizing and to amine oxide; and
    phosphonizing.

14. A process for the preparation of detergent hydrocarbons containing a relatively low amount of isoparaffins comprising separating a hydrocarbonaceous product stream comprising detergent hydrocarbons and hydrocarbons boiling above and below the boiling range of the before mentioned detergent hydrocarbons from a Fischer-Tropsch process using a cobalt based catalyst and producing normally liquid and normally solid hydrocarbons into a light fraction boiling below a fraction comprising detergent hydrocarbons, an intermediate boiling fraction comprising detergent hydrocarbons and a heavy fraction boiling above the intermediate boiling fraction comprising detergent hydrocarbons, the Fischer-Tropsch process being carried out at a pressure above 25 bara.

15. The process of claim 1, in which the Fischer-Tropsch process is carried out at a temperature between 180° C. and 270° C.

* * * * *